Figure 4:
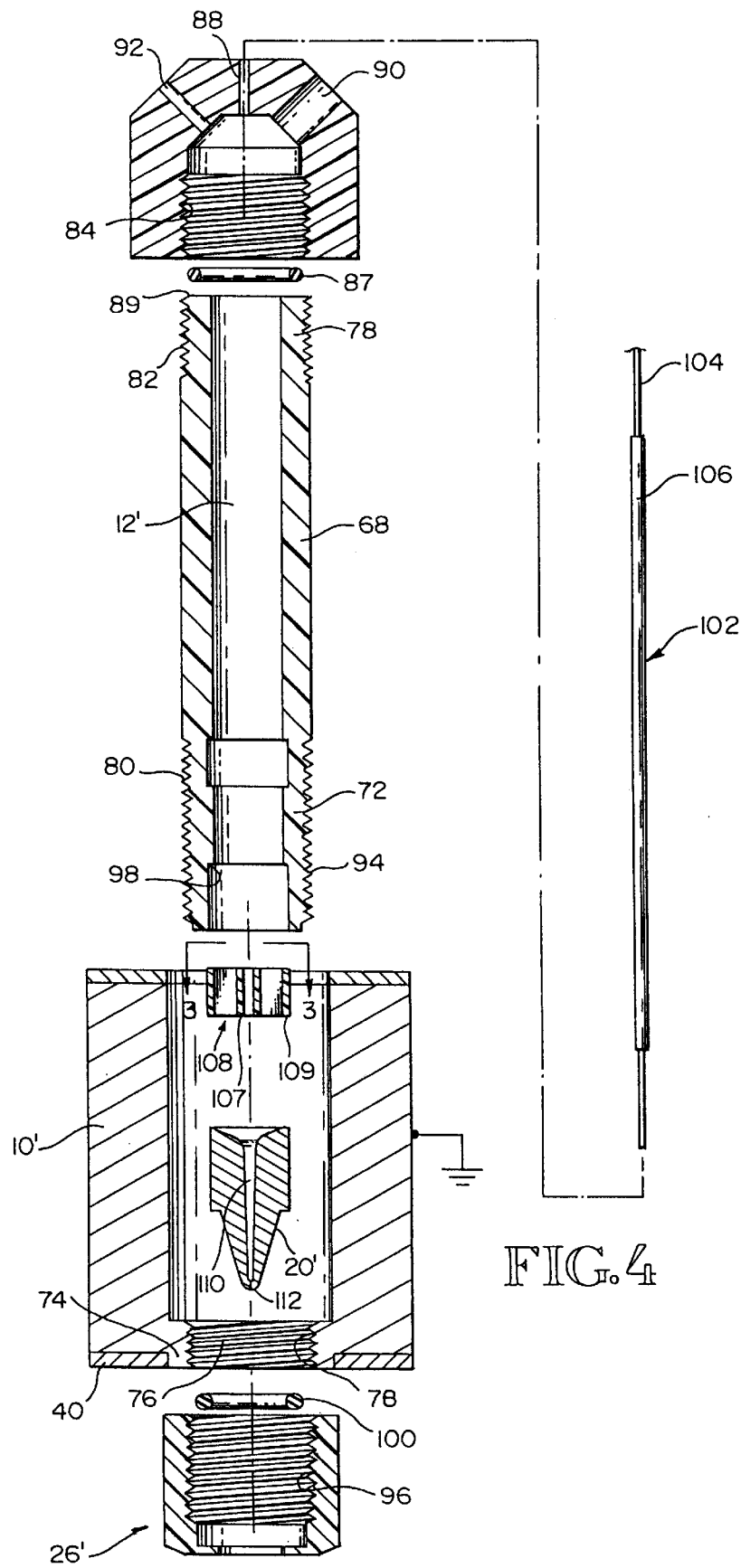

United States Patent [19]
Van den Engh

[11] Patent Number: 6,003,678
[45] Date of Patent: Dec. 21, 1999

[54] PARTICLE SEPARATING APPARATUS AND METHOD

[75] Inventor: Gerrit J. Van den Engh, Seattle, Wash.

[73] Assignee: University of Washington, Seattle, Wash.

[21] Appl. No.: 09/170,017

[22] Filed: Oct. 13, 1998

Related U.S. Application Data

[62] Division of application No. 08/918,695, Aug. 21, 1997, Pat. No. 5,819,948.

[51] Int. Cl.$^6$ ........................................................ B03B 5/66
[52] U.S. Cl. ............................... 209/158; 209/1; 209/2; 209/921; 209/920; 209/3.1; 73/865.5; 324/71.4; 356/441; 356/442
[58] Field of Search ........................... 73/865.5; 324/71.4; 356/441, 442

[56] References Cited

U.S. PATENT DOCUMENTS

| | | | |
|---|---|---|---|
| 3,380,584 | 4/1968 | Fulwyler | 73/865.5 |
| 3,836,912 | 9/1974 | Ghougasian et al. | 364/75 |
| 4,302,166 | 11/1981 | Fulwyler | 425/6 |
| 4,325,483 | 4/1982 | Lombardo et al. | 209/3.1 |
| 4,538,733 | 9/1985 | Hoffman | 209/3.1 |

Primary Examiner—William E. Terrell
Assistant Examiner—Joe Dillon
Attorney, Agent, or Firm—Delbert J. Bernard

[57] ABSTRACT

A disposable first tube (68) extends axially through, and is detachably connected to, an annular main body (10'). An input piezo electric element (38) is attached to a first end of the tubular main body (10'). A second, sensor piezo electric element (40) is attached to the opposite end of the main body (10'). A nozzle (20') having a nozzle passageway (110) and a discharge opening (112) is detachably secured to an outlet end of the first tube (68). A second tube (102) within the first tube (68) delivers a core liquid to the nozzle passageway (110). A sheath liquid is delivered through a space in the first tube (68) surrounding the second tube (102). The nozzle passageway (110) forms the core and sheath liquids into a small diameter jet stream. Electrical energy is delivered to the input piezo electric element (38), to vibrate the nozzle (20') and break the jet stream into droplets. The sensor element (40) determines the amplitude of vibration at the nozzle (20') and delivers this information to a control circuit that adjusts the electrical energy input to the input piezo electric element (38) for maintaining a desired amplitude of vibration at the nozzle (20'). The frequency of vibration is determined by the length of the main body (10') between the two piezo electric elements (38, 40). The first and second tubes (68, 102) are disposable and are replaced after a use rather than being cleaned and sterilized.

8 Claims, 4 Drawing Sheets

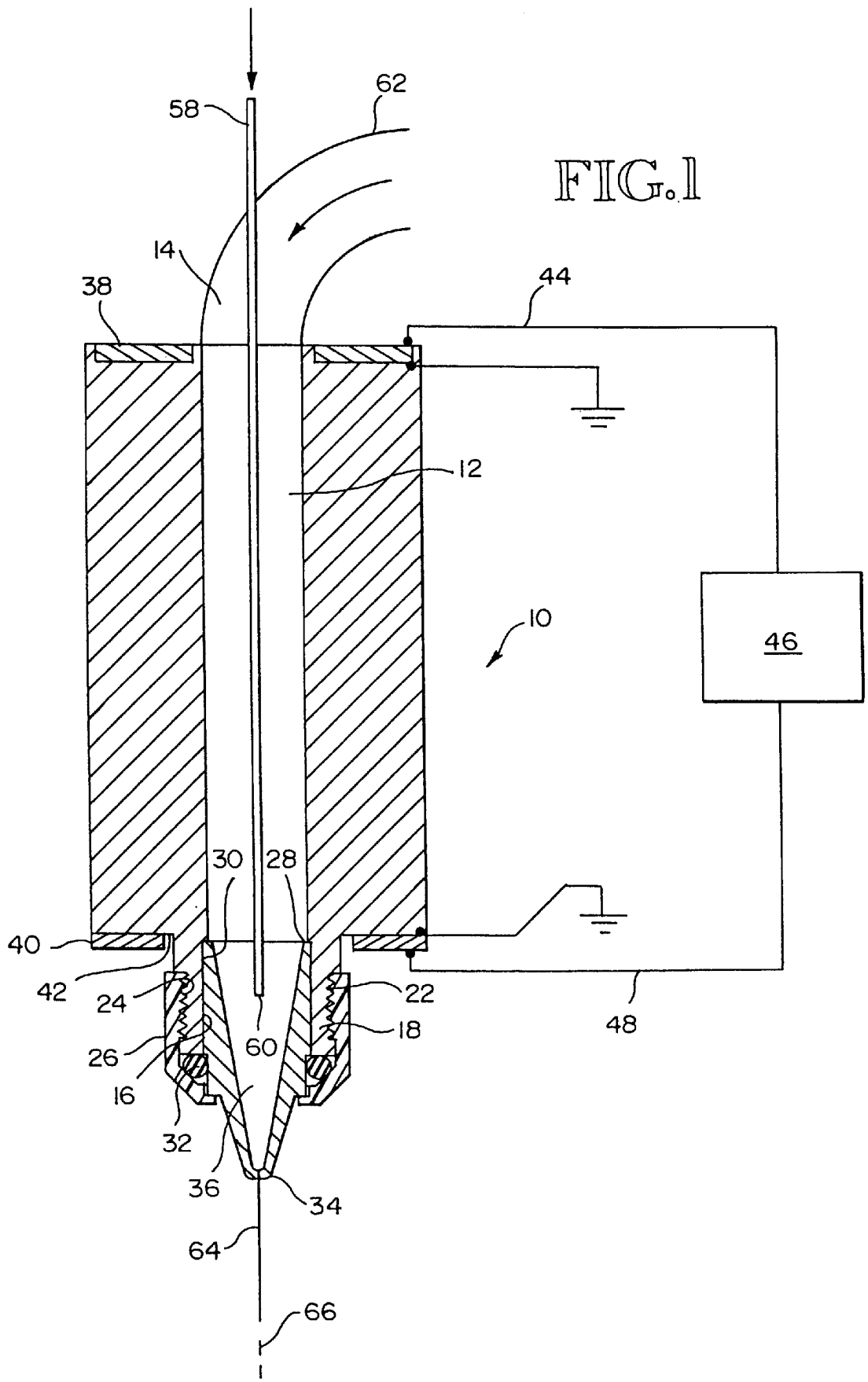

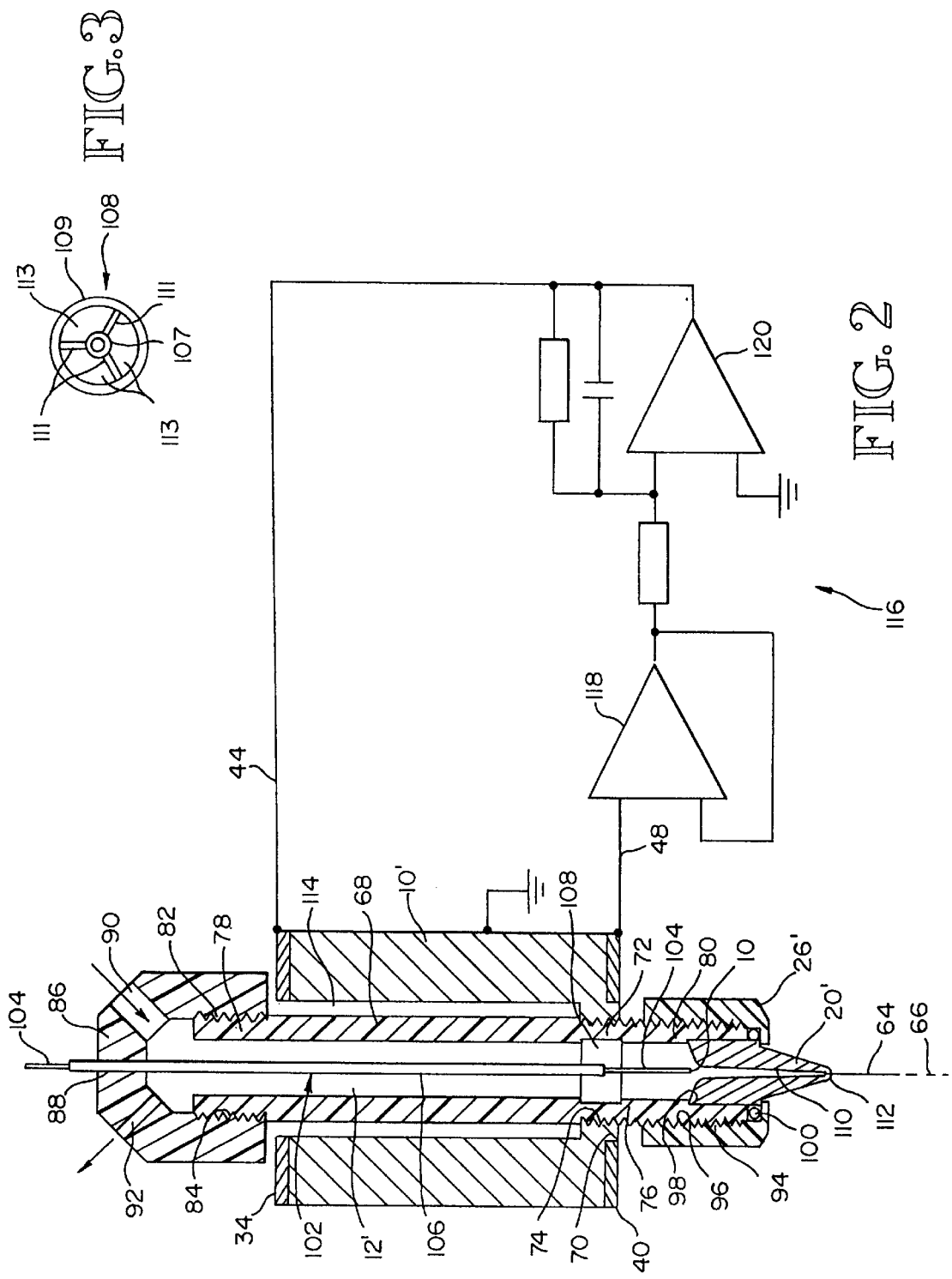

PARTICLE SEPARATING APPARATUS AND METHOD

CROSS REFERENCE TO RELATED APPLICATION

This application is a division of applicant's prior application Ser. No. 08/918,695, filed Aug. 21, 1997, entitled Particle Separating Apparatus And Method, and now U.S. Pat. No. 5,819,948, issued Oct. 13, 1998.

This invention was made with government support under grant number DE-FG06-93ER61662 awarded by the Department of Energy. The government has certain rights in the invention.

TECHNICAL FIELD

The present invention relates to an apparatus and method for separating small particles, by suspending the particles in a liquid, forming the liquid into a small diameter jet stream, and dividing the jet stream into particle carrying droplets. More particularly, it relates to the provision of a particle separator having a main body that functions as a mechanical oscillator and disposable components in contact with the particle carrying liquid, and to separating methods using a mechanical oscillator and disposable components.

BACKGROUND OF THE INVENTION

Known particle separators function to form a particle containing liquid into a small diameter jet stream and then break the jet stream into particle containing droplets. The droplet formation is guided by vibration energy applied to the separator. See, for example, U.S. Pat. No. 4,302,166, granted Nov. 24, 1981, to Mack J. Fulwyler and C. W. William Hatcher, and U.S. Pat. No. 4,361,400, granted Nov. 30, 1982, to Joe W. Gray, Terry W. Alger and David E. Lord.

It is important that the vibration be at a precise, stable frequency. Since the vibration energy determines the break-off point of the droplets, it is important that the energy be constant. In current practice, the vibration frequency is determined by an electronic oscillator that drives a piezo electric element that is incorporated into the separator. There is a need to provide the vibration energy in a way that does not require use of an electronic oscillator because electronic oscillators are expensive. Further, the known apparatuses for forming the droplets have to be cleaned and sterilized between uses. There is a need for a droplet forming apparatus in which at least some of the components that are contacted by the carrier liquid are disposable so that the need to clean and sterilize is significantly reduced, if not eliminated.

It is an object of the present invention to provide a particle separator that is simple, yet durable, inexpensive to make and use, and which includes a mechanical oscillator driven by a piezo electric element to provide substantially constant vibration energy to a nozzle. Another object is to provide a particle separator in which components that are contacted by the particle containing liquid are disposable, so as to at least reduce the need to clean and sterilize between uses. A further object of the invention is to provide a method of droplet formation by use of a mechanical oscillator and components in contact with the particle carrying liquid that are disposable. Yet another object of the invention is to provide a particle separator that is adapted to monitor the vibration energy existing in the particle separator.

Additional prior art particle separators and particle separating methods, present in the patent literature, are disclosed by: U.S. Pat. No. 3,963,606, granted Jun. 15, 1976 to Walter R. Hogg; U.S. Pat. No. 4,325,483, granted Apr. 20, 1982 to Igino Lombardo, Donald E. Barry and W. Peter Hansen; U.S. Pat. No. 5,007,732, granted Apr. 16, 1991, to Hiroshi Ohki, Hideaki Kamohara and Ryo Miyake; U.S. Pat. No. 5,079,959, granted Jan. 14, 1992, to Ryo Miake, Hiroshi Ohki, Isao Yarnazaki, Toshio Kaneko, Hideyuki Horiuchi, Shinich Sakuraba, and Kaori Yasuda; and U.S. Pat. No. 4,538,733, granted Sep. 3, 1985, to Michael A. Hoffman. These patents and the two earlier mentioned patents should be carefully considered for the purpose of putting the subject invention into proper perspective relative to the prior art.

DISCLOSURE OF THE INVENTION

The particle separator of the present invention comprises an axially elongated, tubular main body including a central axial opening and first and second ends. A nozzle at the second end of the tubular main body has a central nozzle passageway and a discharge opening. A sheath liquid passageway and core liquid passageway within the sheath liquid passageway discharge into the nozzle passageway. An input piezo electric element is connected to the first end of the main body and is adapted to vibrate the main body when excited by electrical energy. This causes the main body to function as a mechanical oscillator and vibrate the nozzle. The length of the main body is used to establish the frequency of oscillation.

In one embodiment, the central axial opening in the main body is itself the sheath liquid passageway. In another embodiment, a separate tube extends axially through the central opening in the main body. This separate tube is connected to the main body and provides the sheath liquid passageway. Preferably, the separate tube is detachably connected to the main body and is a disposable component of the separator. Preferably also, a core liquid delivery tube is positioned within the separate tube to form a tube assembly that is disposable.

According to an aspect of the invention, the input piezo electric element is a thin, annular member that is bonded to the first end of the tubular main body.

According to another aspect of the invention, a second piezo electric element is connected to the second end of the tubular main body. Preferably, the second piezo electric element is a thin, annular member that is bonded to the second end of the tubular main body.

In use, a particle containing core liquid is introduced through the core liquid passageway. At the same time, a sheath liquid is introduced into the sheath liquid passageway. The geometry of the nozzle passageway forms the core and sheath liquids into a small diameter jet stream that discharges from the discharge end of the nozzle. Electrical energy is applied to the input piezo electric element in an amount sufficient to cause it to vibrate the separator and cause the jet stream to break up into droplets. The frequency of vibration is a function of the length of the tubular main body between the two piezo electric elements. It is selected to produce a vibration level sufficient to effect the desired droplet formation. The sensor piezo electric element is used to sense the amplitude of vibration at the nozzle and send a feedback signal to a control circuit. The control circuit adjusts the electrical energy delivery to the input piezo electric element, to maintain the desired level of vibration at the nozzle. The circuit also sets the phase shift and frequency of the feedback signal.

In a preferred embodiment, which includes the disposable tube that is detachably connected to the main body, after a use the separator is dismantled, the disposable tube is discarded, and a new disposable tube is installed in its place.

Other advantages, objects and features will become apparent from the following best mode description, the accompanying drawings, and the claims, which are all incorporated herein as part of the disclosure of the invention.

BRIEF DESCRIPTION OF THE DRAWINGS

Like reference numerals are used to designate like parts throughout the several views of the drawing, wherein:

FIG. 1 is a longitudinal sectional view of a first embodiment of the invention, including a schematic showing of a basic control circuit;

FIG. 2 is a view like FIG. 1 but of a second embodiment of the invention, and including a more detailed schematic diagram of a control circuit;

FIG. 3 is a cross-section view taken along line 3—3 of FIG. 4;

FIG. 4 is an exploded pictorial view of the particle separator of FIG. 2; and FIG. 5 is a view like FIG. 1 but of a third embodiment of the invention

BEST MODE FOR CARRYING OUT THE INVENTION

The particle separator shown by FIG. 1 includes a tubular main body 10 defining a central axial passageway 12 having an inlet end 14 and an outlet end 16. Body 10 is made from a solid material: metal, plastic, ceramic, etc. At the outlet end, the outside diameter of body 10 is reduced to form a tubular end portion 18 to which a nozzle tip 20 is secured. External threads 22 on body end portion 18 mate with internal threads 24 formed within a nozzle tip retainer nut 26. Inside body end portion 18, the internal diameter of passageway 12 is enlarged and a radial shoulder 28 is formed. As illustrated, the inner end of nozzle tip 20 fits into passageway 12 and contacts shoulder 28. An O-ring seal 32 is positioned radially between nozzle tip 20 and retainer nut 26 and axially between body end portion 18 and a radial end wall at the outer end of retainer nut 26. When nozzle tip 20, retainer nut 26 and O-ring seal 32 are installed, a rotation of the retainer nut 26, to screw it onto the threads 22, will compress the O-ring 32. The compressed O-ring provides a liquid seal between the nozzle tip 20 and the body end portion 18. Nozzle tip 20 includes an axial passageway 34 that forms a continuation of the passageway 12 in body 10. Passageway 34 converges from where the end 30 of nozzle tip 20 contacts the shoulder 28 to a discharge opening 36.

In the FIG. 1 embodiment, a first piezo electric element 38 is connected to the inlet end of body 10. A second piezo electric element 40 is connected to the outlet end of body 10. Specifically, piezo electric element 38 is connected to a radial end surface. Piezo electric element 40 is connected to a radial shoulder 42 formed where the main portion of body 10 meets the body end portion 18. Piezo electric elements 38, 40 may be in the form of thin annular rings that are available from American Piezo Ceramics, Ind., of Mackeyville, Pa.: e.g. Models R: 84-015-850 or R: 8-4-040-850. The connection may be by bonding, by use of an adhesive resin. Piezo electric element 38 is an input element and may be termed a "signal piezo electric element." Piezo electric element 40 is a sensor element and may be termed a "sensor piezo electric element." A conductor 44, leading from a control circuit 46, brings electrical energy to the piezo electric element 38. A conductor 48, leading from the piezo electric element 40, conducts an electrical feedback signal back to the circuit 46 for reasons that will hereinafter be described.

In the system of FIG. 1, the tubular main body 10 may be constructed from a conductive material or a nonconductive material. If the material is nonconductive, each of the piezo elements 38, 40 must be connected to ground. In FIG. 1, the inside surfaces of the piezo elements 38, 40 are shown to be connected to ground. If body 10 is constructed from a conductive material, e.g. metal, a single ground is sufficient. This is shown in FIGS. 2, 4 and 5. In those systems, the bodies 10', 124 are shown to be connected to a single ground wire.

There is a benefit to be gained by the use of a second piezo element 40, even if it is not part of a feedback loop. The second piezo element 40 makes it possible to monitor the vibration energy. It can be used to register the vibration intensity.

A liquid delivery tube 58 extends into and partially through passageway 12. Tube 58 has a discharge opening 60 that may terminate at a location within the converging passageway 38 in nozzle tip 20. A sheath liquid delivery tube 62, shown in schematic form in FIG. 1, is provided to deliver a sheath liquid to the inlet 14. In use, a particle carrying core liquid is introduced into the delivery tube 58 and a sheath liquid is introduced into the inlet tube 62 and passageway 12. The internal geometry of body 10 and nozzle tip 20 forms the core and sheath liquids into a particle carrying liquid jet stream that is discharged from opening 36. Piezo electric element 38 is energized to vibrate body 10 within the range of the natural frequencies of the liquid jet stream 64. This causes the liquid jet stream 64 to break up into regular segments or droplets 66.

FIGS. 2–4 show a second embodiment of the invention. It is characterized by an elongated tube 68 within a tubular body 10'. Tube 68 provides a sheath liquid passageway 12'. Tube 68 includes an inlet end portion 70 that projects axially outwardly from the inlet end of the body 10 and an outlet end portion 72 that projects axially outwardly from the outlet end of the body 10'. The outlet end of the body 10' includes an inwardly directed radial flange 74 forming a circular opening 76. The periphery of the opening 76 includes internal threads 78. These internal threads 78 mate with external threads 80 on tube 68. End portion 70 includes external threads 82 that mate with internal threads 84 in a cap 86. A seal ring 87 is positioned between the upper end 89 of tube 68 and a shoulder within cap 86 at the base of threads 84. Cap 86 includes a core liquid delivery tube receiving opening 88, a sheath liquid inlet 90 and an air vent 92. When cap 86 is rotated to tighten it on the threads 82, the seal ring 87 is compressed to provide a liquid seal. End portion 72 includes external threads 94 that mate with internal threads 96 within a nozzle tip retaining nut 20'. As in the first embodiment, the inner end of a nozzle tip 25 fits into the passageway 12' and abuts against a shoulder 98 formed within end portion 72 of tube 68. A seal ring 100 is positioned between an outer end portion of retainer nut 26' and a shoulder on nozzle tip 20'. When retainer nut 26' is rotated to tighten it on the threads 94, the seal ring 100 is compressed. The compressed seal ring 100 provides a liquid seal that prevents leakage of the sheath liquid through the connection of the nozzle tip 20' to the tube 68.

A core liquid delivery tube 102 extends through the opening 88 into and partially through the passageway 12'. Tube 102 may be of two-part construction. It may comprise a plastic inner tube 104 and a shorter metal outer tube 106 closely surrounding tube 104. A spacer 108 is provided within passageway 12'. Spacer 108 has a central hub portion 107 (FIG. 3) through which tube 102 extends, an outer ring portion 109, and a plurality of radial spokes 111 (e.g. three) extending between the hub 107 and ring portion 109. Spaces 113 between the spokes 111 provide flow paths for the sheath liquid. In this embodiment, the discharge end 105 of tube 104 is placed closely adjacent the inlet of the passageway 110 in nozzle tip 20'. This passageway 110 includes a discharge opening 112 through which a jet stream is discharged.

As shown in FIGS. 2 and 3, the tube 68 is connected to the body 10' by the mating threads 74, 76. This connection is at the outlet end of the body 10'. The opposite or inlet end of the body 10' is not connected to the tube 68. Rather, tube 68 extends axially through center opening 114 in tubular body 10' in a spaced relationship to the sidewall portion of the body 10'. End member 86 is connected to tube 68 in an axially spaced relationship which the body 10'.

In the embodiment of FIGS. 2 and 3, some of the components may be disposable. These may include tube 68, tube 106, end cap 86, and spacer 108 and may also include retainer nut 26'. These disposable parts are constructed from a plastic material with the exception of delivery tube 102 that may include a metal sheath 106. The disposable or throw-away nature of these parts make it unnecessary to wash and sterilize these parts because they are not reused. Body 10' is not disposable. Retainer nut 26' and nozzle tip 20' may also be not disposable.

As in the first embodiment, an input piezo electric element 38 is connected to the input end of main body 10'. A sensor piezo electric element 40 is connected to the outlet end of body 10'. The connections may be by bonding, by the use of a suitable resin adhesive. As in the first embodiment, a first conductor 44 is connected to piezo electric element 38. A second conductor 48 is connected to piezo electric element 40. A control circuit 116 is positioned between the conductors 44, 48. In both embodiments, the tubular body 10 functions as a mechanical oscillator. Electrical energy applied to piezo electric element 38 will cause body 10 to alternatively lengthen and shorten at a frequency established in part by the length of body 10. This feature eliminates the need of a separate expensive electronic oscillator.

In cell separating, the cell particle carrying core liquid, and the sheath liquid, are forced through a small orifice (34, 112) to form a liquid jet stream (64) in air. The jet stream is subjected to a vibration within the range of natural frequencies of the jet stream. This causes the jet stream to break up into regular droplets (66). The cell particles are in the droplets. The cell separator must satisfy several demands. The flow of liquid must be laminar. The sample substance must be introduced at the core of the liquid jet stream. The separator must transfer a vibration to the liquid jet stream. In separators constructed in accordance with the invention, the vibration is caused by a piezo electric element driven by an electrical signal. The efficiency of coupling between the piezo electric elements vibration and the liquid jet stream depends on the "Eigen frequencies" in the separator structure. Resonant modes in the separator structure may cause certain frequencies either to be amplified or to be attenuated. The ideal separator has few resonant modes so that frequencies over a wide range are equally effective. In that case, the vibration of the input piezo electric element can be set at the natural frequency of droplet formation of the liquid jet without having to consider the particular behavior of the separator structure at that frequency.

The vibration can be added as an acoustical wave. The behavior of the acoustical wave is affected by reflections from boundaries inside the separator structure. It is best to couple the vibrations to the separator body. To minimize reflections, the vibration should be parallel to the liquid flow. A separator body in the form of a solid cylinder surrounding the flow channel is most effective. The input piezo electric element is a ring through which the liquid passageway extends. To minimize reflections, the electric element should be at an end of the separator body. To minimize side-resonant modes, it is best to make the separator body longer than wide. In that case, the dominant resonance is caused by reflections from the nozzle end of the separator body. If the desired frequency range is known, the length of the separator body can be chosen so that the reflection from the nozzle end of the body is approximately in phase with the input signal. This results in the separator structure vibrating very efficiently over a range around the normal frequency. If a frequency response over a wider range is desired, the separator body can be given a tapered shape. In such a nozzle, the input piezo electric element is attached to the end of the separator body opposite the nozzle, i.e. opposite the discharge of the fluid jet. The separator body tapers towards the discharge nozzle.

A separator main body having a right cylindrical shape, such as shown by FIGS. 1, 2 and 4, has the advantage that a second, sensor piezo electric element can be mounted on the second end of the separator body 101. This second piezo electric element generates a voltage signal related to the strength of the vibration in the separator structure. This voltage signal can be used in a feed-back loop to keep the strength of the vibration at the discharge end of the nozzle substantially constant. For example, temperature changes will not change the frequency but will change the amplitude of vibration. The feedback circuit can be used to make electronic energy input adjustments in order to maintain the amplitude substantially constant.

A prototype of the FIG. 2 system was built and tested. The length of the main body 10' was about 35 mm. The natural resonance frequence was about 70 kHz. A fluid pressure of 30 psi was used to form a 70 micrometer jet stream. This system functioned to form a very stable stream of droplets. The feedback loop included a follower 118, an inverter 120 and a low-pass RC sorter. The phase-shift of the feedback loop was ninety degrees (90°). The electronic circuit 116 picked up the vibrations from sensor piezo electric element 40 (the vibration signal) and fed them back to the signal piezo electric element 38 (the vibration source). The system 116 had an oscillator frequency that was determined by the length of the main body 10' and the phase-shift of the feedback loop. Amplification of the circuit that drives the vibration as voltage dependent. This allowed the amplitude of the vibration signals to be maintained at a constant level. The oscillator had a very stable frequency (drift <<1:1000). The feedback loop maintained a constant vibration level.

Figure 5:
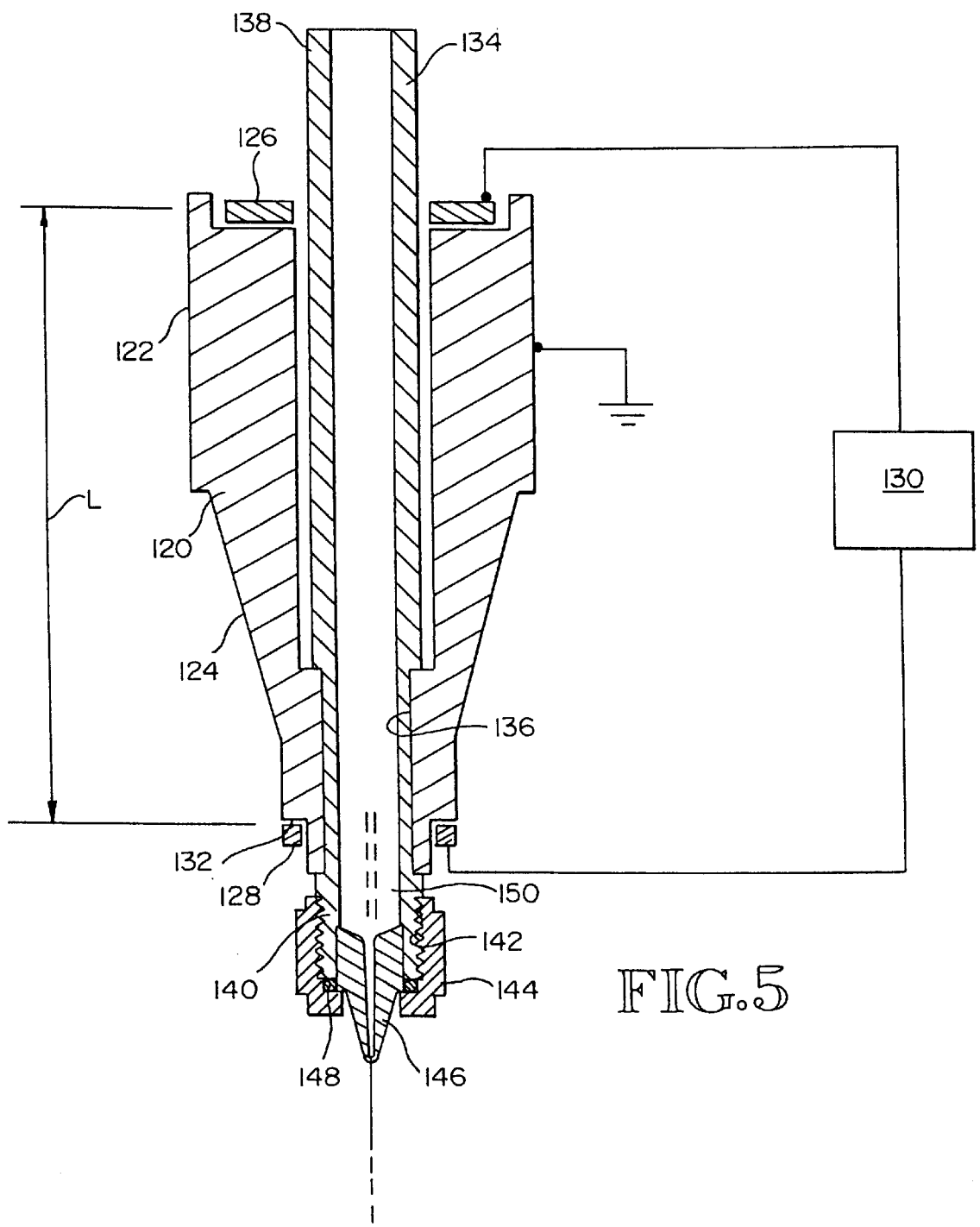

The embodiment of FIG. 5 includes a body 120 having a right cylindrical inlet end portion 122 and a tapered outlet end portion 124. The taper results in a dampening of undesirable transverse and complex wave generation. It promotes wave generation that is parallel to fluid flow through the separator. As in the earlier embodiments, the FIG. 5 embodiment includes a signal piezo electric element 126 and a sensor piezo electric element 128, interconnected by a feedback circuit 130. The signal piezo electric element 126 may be a thin annular member that is bonded to the inlet end of body 120. The sensor piezo electric element 128 may be an annular element that is bonded to a shoulder 132 that is formed near the nozzle end of the body 120. The frequency of vibration is a function of the length of the body 120 between the two piezo electric elements 126, 128.

The FIG. 5 embodiment may include a disposable center tube 134 that is thread connected at 136 to the body 120. The upper end portion 138 of tube 134 may be threaded to receive an inlet cap-like cap 86 in the FIG. 4 embodiment. The opposite end 140 of tube 134 is thread connected at 142 to a nozzle tip retainer nut 144. Nut 144 holds a nozzle tip 146 in place at the lower end of tube 134. As in the earlier embodiment, an O-ring 148 is provided to seal against leakage between retainer nut 144 and the end of tube 134. As in the earlier embodiments, the FIG. 5 embodiment includes a core liquid delivery tube 150. It may be like the core liquid delivery tube 102 that is a part of the FIG. 4 embodiment. For this reason, only a discharge end portion of the tube 150 is illustrated and it is shown by broken lines. The FIG. 5 embodiment is believed to be the preferred embodiment.

The illustrated embodiments are only examples of the present invention and, therefore, are non-limitive. It to be understood than many changes in the particular structure, materials and features of the invention may be made without departing from the spirit and scope of the invention. Therefore, it is my intention that my patent rights not be limited by the particular embodiments illustrated and described herein, but rather determined by the following claims, interpreted according to accepted doctrines of claim interpretation, including use of the doctrine of equivalents and reversal of parts.

What is claimed is:

1. A particle separator, comprising:
   an axially elongated, tubular main body having a central axial opening and first and second ends;
   a separate tube extending axially through the central axial opening in said main body, said tube being connected to the main body and defining a sheath liquid passageway, said separate tube including a sheath liquid inlet and an outlet;
   a nozzle at the outlet of the separate tube, said nozzle having a central nozzle passageway and a discharge opening, said sheath liquid passageway discharging into said nozzle passageway;
   a core liquid passageway in said sheath liquid passageway, said core liquid passageway having a discharge opening discharging into the nozzle passageway;
   an input piezo electric element connected to the first end of said tubular main body and adapted to vibrate said main body when excited by electrical energy, whereby said main body will function as an oscillator; and
   a second piezo electric element connected to the second end of the tubular main body, said second piezo electric element functioning to generate a voltage signal related to the strength of the vibration in the assembly body,
   wherein the length of the tubular main body between the two piezo electric elements establishes the frequency of vibration.

2. A particle separator according to claim 1, wherein said outlet of said separate tube includes an outlet portion extending axially outwardly from the second end of the tubular main body, and said nozzle is a separate structure that is detachably connected to the outlet portion of said separate tube.

3. A particle separator according to claim 1, further comprising a screw connection between the separate tube and the tubular main body, at the second end of the main body, said tube extending from such connection through the central axial opening, in a radially spaced relationship to said opening.

4. A particle separator according to claim 3, wherein said separate tube includes an inlet portion that projects axially outwardly from the first end of the tubular main body, said particle separator including an end cap connected to said inlet portion, said end cap including a sheath liquid inlet.

5. A particle separator according to claim 4, said separate tube further comprising a small diameter tube structure that defines the core liquid passageway, said tube structure extending axially through said separate tube, and wherein the inlet cap includes an opening to which said tube structure extends.

6. A method of forming droplets, comprising:
   providing an axially elongated, tubular main body having a central axial opening and first and second ends;
   providing a sheath liquid passageway within the tubular main body extending from the first end to the second end;
   providing a core liquid passageway in said sheath liquid passageway;
   providing a nozzle having a central nozzle passageway and a discharge opening;
   providing the core liquid passageway with a discharge opening and positioning it to discharge core liquid into the nozzle passageway;

providing the sheath liquid passageway with a discharge opening and positioning it to discharge a sheath liquid into the inlet of the nozzle passageway, in a surrounding relationship to the discharging core liquid;

introducing a core liquid into the core liquid passageway and a sheath liquid into the sheath liquid passageway;

configuring the nozzle passageway so that the core liquid and the sheath liquid are formed by said nozzle into a small diameter jet stream that discharges from the discharge opening of the nozzle;

providing an input piezo electric element and connecting to the first end of said tubular main body;

applying electrical energy to the input piezo electric element so as to vibrate the tubular main body, and cause it to function as a mechanical oscillator, for vibrating the nozzle so as to cause vibrations that will break the jet stream into droplets; and establishing a frequency of vibration by a selection of the length of the tubular main body.

7. A method of claim 6, further comprising connecting a sensor piezo electric element to the second end of said tubular main body, and using said sensor piezo electric element to determine the amplitude of vibration of the nozzle, and using the amplitude of vibration as a feedback control signal, for adjusting the electrical energy input to the input piezo electric element for the purpose of maintaining a desired vibration energy at the nozzle.

8. The method of claim 6, comprising providing an elongated first tube, extending said first tube through the central axial opening in the tubular main body, and detachably connecting said first tube to the tubular main body;

providing a second smaller tube within the first tube;

using the smaller second tube to provide the core liquid passageway;

using an annular space that is defined by and between the first and second tubes to provide the sheath liquid passageway;

detachably connecting the nozzle to the first tube; and following the formation of droplets, disconnecting the first tube from the tubular main body and the nozzle from the first tube, disposing the first tube, and replacing the disposed first tube with a new first tube.

* * * * *